United States Patent [19]

Ueberschaer

[11] 4,326,427
[45] Apr. 27, 1982

[54] LIQUID SAMPLING GAUGE APPARATUS

[75] Inventor: Hubert J. Ueberschaer, Hartsdale, N.Y.

[73] Assignee: Mobil Oil Corporation, New York, N.Y.

[21] Appl. No.: 221,239

[22] Filed: Dec. 30, 1980

Related U.S. Application Data

[63] Continuation-in-part of Ser. No. 124,015, Feb. 25, 1980, abandoned.

[51] Int. Cl.³ .............................................. G01N 1/12
[52] U.S. Cl. ................................................. 73/864.65
[58] Field of Search ........... 73/864.63, 864.65, 864.61; 33/126.4 R, 126.4 A

[56] References Cited

U.S. PATENT DOCUMENTS 2,203,019 6/1940 Johnson et al. .................. 73/864.65
2,678,563 5/1954 Parrish ............................ 73/864.65

FOREIGN PATENT DOCUMENTS 566752 1/1945 United Kingdom ............. 73/864.65

*Primary Examiner*—S. Clement Swisher
*Attorney, Agent, or Firm*—Charles A. Huggett; Michael G. Gilman; James F. Powers, Jr.

[57] ABSTRACT

A liquid-sampling gauge for obtaining a sample of liquid (e.g. water) from on or near the bottom of a liquid-filled container having one or more layers of liquid therein (e.g. a crude oil or other refined oil-filled cargo tank) and for determining the depth of the bottom layer (e.g. water) in the container. The gauge is comprised of a cylinder which is effectively open at its upper end and closed at its lower end. A spring-biased valve normally closes an inlet opening through the lower end of the cylinder. The sampling apparatus may be used with either the cylinder initially empty or filled with a fluid such as water. If the cylinder was initially empty it fills with fluid, e.g. oil, through its open upper end as it is lowered into the liquid-filled container. As the cylinder reaches bottom, a valve actuator on the cylinder engages the bottom of the container and continued downward movement of the cylinder opens the valve which allows displacement activity to occur. Flow will continue until the interface level inside the cylinder equals the level of the water layer in the container. Upon lifting of the cylinder, the spring-biased valve closes thereby trapping the water in the cylinder for retrieval, measurement and analysis.

10 Claims, 4 Drawing Figures

LIQUID SAMPLING GAUGE APPARATUS

CROSS-REFERENCE TO RELATED APPLICATION

This is a continuation-in-part of application Ser. No. 124,015, filed Feb. 25, 1980, now abandoned.

BACKGROUND OF THE INVENTION

The present invention relates to an apparatus for obtaining a sample of liquid from near the bottom of a liquid-filled container and more particularly relates to a liquid sampling gauge apparatus for obtaining a sample from a layer of water or water-oil emulsion underlying crude oil in a cargo tank and for determining the depth of said layer.

In many instances, cargo oil, e.g. crude or refined oil which is loaded onto tanker ships, is contaminated with substantial amounts of water. Because of differences in certain physical properties such as density and specific gravity, oil forms the top layer. One cannot readily ascertain how much oil or water is in a cargo tanker by mere visual inspection, and it can be easily understood that if payment for the purchased oil is based on the measured volume of total liquid in the cargo tanks, the final cost to a buyer may be substantially inflated since he pays for the useless water at cargo oil prices. In many actual cargo oil purchasing situations existing today, the buyer is allowed to deduct the volume of water in the cargo tanks only if he can prove that it was pumped aboard with the cargo oil and was not already present in the tanks before the cargo oil was loaded.

Since water inadvertently left in the tanks (e.g. seawater used for ballast, etc.), will have a substantially different composition from the water loaded with the cargo oil (e.g. formation water produced with the crude oil or condensate from steam used in processing the produced oil, etc.), the origin of the water in question can readily be established if a sample of the water can be obtained from a cargo tank for analysis after it has been loaded.

Further, by knowing the origin of any water in a loaded cargo tank, steps can be taken to alleviate the contamination problem. That is, if the water is being pumped in with the cargo oil, further processing of the cargo oil can be undertaken to remove the water before loading, or if the water is originally present in the tank, further steps can be taken aboard the ship to remove such water before loading. Also, it is necessary to determine the depth of the water layer so that the volume of water in the filled tank can be deducted from the total volume of liquid in the tank. Therefore, it can readily be seen that an important need exists both for obtaining a sample of any water that may be present in a cargo tank after it has otherwise been loaded with crude or refined oil, and for determining the depth of said water in the tank.

Several sampling devices have been proposed for this purpose. For example, in copending U.S. patent application Ser. No. 937,293, filed Aug. 2, 1978, a sampling device is disclosed which is comprised of a flexible conduit, normally closed at its upper end. The conduit is lowered with a sounding bob into a filled cargo tank until the lower end of the conduit is positioned within the water layer on the bottom of the tank. The conduit is then opened and suction is applied to withdraw a sample of the water through the conduit. Another sampling device of this general type is disclosed in copending U.S. patent application Ser. No. 68,995, filed Aug. 23, 1979. This sampling device is comprised of a cylinder having a piston positioned therein. The cylinder is lowered on a line into the liquid to be sampled. The line is then lifted to raise the piston relative to the cylinder to draw the liquid to be sampled into the cylinder.

Other known sampling devices for obtaining samples from a liquid-filled tank are disclosed in U.S. Pat. Nos. 1,511,591; 2,593,830; and 3,129,513; all of which disclose lowering a device comprising either an open tube or cylinder into a liquid-filled tank and then closing a valve at the lower end of the tube or cylinder once the device is in place to trap a sample of fluid therein for retrieval.

SUMMARY OF THE INVENTION

The present invention provides a simple, self-contained apparatus for (1) obtaining a sample of liquid from a liquid layer on or near the bottom of a liquid-filled container such as the cargo tank of an oil tanker and (2) determining the depth of said liquid layer. More specifically, the present liquid sampling gauge is comprised of a transparent cylinder having a top and bottom plate thereon. The top plate has openings therethrough which make the cylinder effectively open at its top. The bottom plate has an inlet opening therethrough which is normally closed by a spring-biased valve mounted on the bottom plate. An actuator plate having a valve lifter thereon is slidably mounted on the bottom plate.

In operation, the liquid sampling gauge is lowered into the container on a line. As the sampling gauge descends, the cylinder will fill with liquid from the container through the openings in the top plate. When the actuator plate engages the bottom of the container, the cylinder will continue to move downward under its own weight with relation to said actuator plate whereby the valve lifter on the actuator plate will open the valve. In a system comprising, for example, an oil layer and a water layer this opening of the bottom valve allows the liquid from the liquid layer at the bottom of the container (e.g. water in a water/oil system) to displace the liquid already in the cylinder until the level inside the cylinder equals the depth of the layer of the sampled liquid. If the cylinder was filled with oil during the lowering of the apparatus through the container, then the opening of the spring-biased valve at the bottom of the gauge allows water to enter through the bottom of the apparatus thereby displacing a portion of the oil until the level of water in the gauge is the same as the level of water in the container outside of the gauge. After sufficient time for equilibration is allowed the apparatus is raised from the bottom of the container, whereby the spring-biased valve is closed and the sampled liquid is trapped in the gauge. When the sampling gauge is lifted off the bottom of the container the bottom plate moves upward in relation to the actuator plate so that the valve lifter moves out of contact with the valve thereby allowing the spring to close the valve. The sampled liquid is trapped in the cylinder for measurement and analysis after the sampling gauge is removed from the container.

In a more preferred method of operation the apparatus is first filled with water. The apparatus is then lowered to the bottom of the container. The weight of the apparatus opens the spring-biased valve mounted on the bottom plate. When the valve on the bottom plate is opened a portion of the water in the cylinder is displayed by oil entering through the openings in the top plate until the level of water in the gauge is the same as the level of the water in the container outside of the gauge. As previously described, time for equilibration of the liquid levels is allowed and the apparatus is then raised from the bottom of the container. There is little or no problem with compensating for any emulsion layer in determining the level of the bottom layer of liquid.

BRIEF DESCRIPTION OF THE DRAWINGS

The actual construction, operation, and the apparent advantages of the present invention will be better understood by referring to the drawings in which like numerals identify like parts and in which.

DESCRIPTION OF THE PREFERRED EMBODIMENTS

Figure 2:
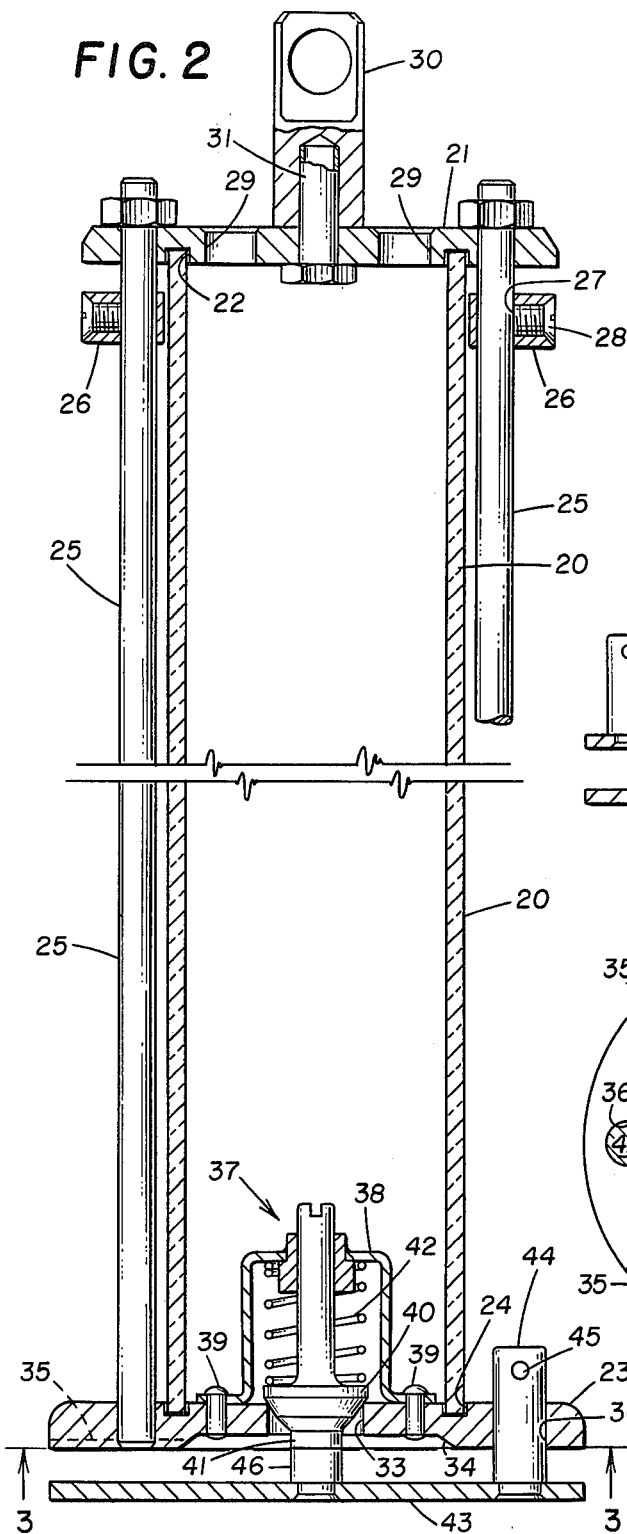
FIG. 2 is a section view, partly broken away, of the liquid sampling gauge apparatus of the present invention.
Figure 1:
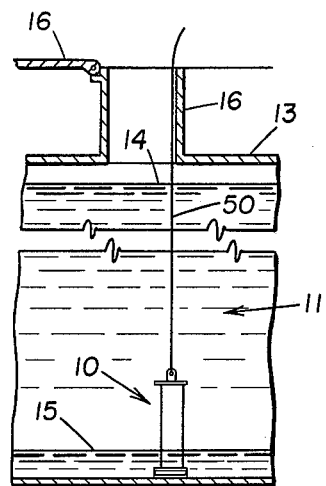
FIG. 1 is a partial vertical sectional view of the present invention in an operable position within a crude oil cargo tank.

Referring more particularly to the drawings, FIG. 1 discloses a liquid sampling gauge apparatus 10 in an operable position within cargo tank 11 of a tanker ship or the like. Tank 11 has a bottom 12 and a top normally formed by deck 13 and is shown substantially filled with cargo oil 14 which has an underlying layer 15 of water and/or water oil emulsion therein. Hatch 16 on deck 13 provides entry into tank 11.

Sampling gauge apparatus 10 is comprised of an elongated cylinder 20 which is preferably made from a sturdy, transparent material such as polymethylmethacrylate, e.g. Plexiglas ® (Rohm & Haas Co.); or other acrylic resins, e.g. Lucite ® (DuPont & Co.). Top closure member, e.g. top plate 21 has a circumferential groove 22 therein which receives the upper end of cylinder 20. Bottom closure member, e.g. bottom plate 23 has a circumferential groove 24 therein which receives the lower end of cylinder 20. Top plate 21 and bottom plate 23 are held in place on cylinder 20 by a plurality of tie rods 25 which secure the two plates together. Also, when assembled, tie rods 25 provide protection for cylinder 20 from accidental scratching, fracturing, or the like during handling or storage of sampling gauge 10. An alignment ring 26 may be provided near the upper ends of tie rods 25 which has openings 27 therethrough spaced to properly align tie rods 25 before assembling top plate 21 thereon. Ring 26 is held in place on tie rods 25 by means of set screws 28 or the like.

A plurality of openings 29 are provided through top plate 21 for a purpose described below. Eye 30 is also provided on the upper surface of top plate 21 and is shown as being attached thereto by means of bolt 31 or the like. However, it should be understood that eye 30 could be made integral with top plate 21 or attached thereto by any known means, e.g. welding.

Figure 3:
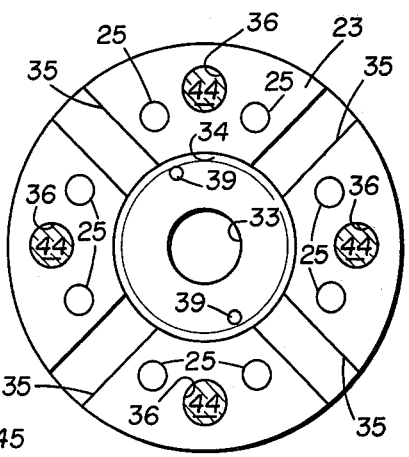
FIG. 3 is a cross-sectional view taken along line 3—3 of FIG. 2.

Bottom plate 23 has a plurality of tapped holes (FIG. 3) properly spaced to receive the lower ends of tie rods 25. Plate 23 also has an inlet opening 33 therethrough which fluidly communicates with recess 34 which, in turn, is formed on the lower surface of plate 23. Radial grooves 35 are formed on the lower surface of plate 23 and extend from the outer circumference of plate 23 into recess 34 thereby providing fluid passages across the bottom of plate 23 as will be described in more detail below. A second plurality of openings 36 are formed through plate 23 for a purpose described below.

Valve means 37 is affixed to the upper surface of bottom plate 23 and is adapted to normally close inlet opening 33. Valve means 37, as illustrated, is comprised of support means 38 which is affixed to plate 23 by pins 39 or the like. Valve 40 is slidably mounted in cage 39 and seats with inlet opening 33 to close same. The lower end 41 of valve 40 extends through inlet opening 33 and terminates approximately even with the lower surface of plate 23. Spring 42 normally biases valve 40 to a closed position.

Valve actuator plate 43 has a plurality of guide pins 44 spaced thereon which are adapted to be slidably received by openings 36 through plate 23. Guide pins 44 are positioned in their respective openings 36, and roll pins 45 or the like are placed through guide pins 44. This limits downward movement of guide pins 44 and thereby retains actuator plate 43 on bottom plate 23 during the lowering and lifting of sampling gauge 10. Valve lifter 46 is positioned on the upper surface of actuator plate 43 and is affixed thereto peening, welding or the like.

A variety of materials may be used for the components of the gauge if means are included to weight the apparatus so it will sink to the bottom of the container. Due to the potentially corrosive nature of some of the materials to which the apparatus may be exposed (e.g. sea water) and the desirability of imparting some weight to the apparatus so that it will sink to the bottom of a deep container such as a tanker, it is preferred that brass or corrosion-resistant stainless steel be used for all portions comprising the apparatus except the transparent cylinder.

In one method of opertion, line 50, e.g. thin braided wire (FIG. 1), is attached to eye 30 and sampling gauge 10 is lowered into cargo tank 11. Inlet opening 33 on bottom plate 23 is closed by valve 40 due to the bias of spring 42. As sampling gauge 10 is submerged in the oil 14, cylinder 20 will fill with oil through openings 29 in top plate 21. When sampling gauge 10 reaches the bottom 12 of tank 11, valve actuator plate 43 comes to rest on bottom 12. Due to its own weight, cylinder 20 continues downward movement on the guide pins 44 of actuator plate 43 whereby valve lifter 46 engages and opens valve 40.

Water from layer 15 then flows through grooves 35 on bottom plate 23 and into cylinder 20 through inlet opening 33. The water continues to displace the oil in cylinder 20 through openings 29 in top plate 21 until the interface level within cylinder 20 equals the depth of the surrounding water layer 15 in tank 11. To insure that the level of water inside cylinder 20 is equalized with the depth of layer 15, sampling gauge 10 is left at rest on bottom 12 for at least 60 seconds.

Alternatively, in a more preferred method of operation, a liquid sampling gauge 10 is first filled with water before it is lowered into cargo tank 11. Inlet opening 33 on bottom plate 23 is closed by valve 40 due to the bias of spring 42. When sampling gauge 10 reaches the bottom 12 of tank 11, valve actuator plate 43 comes to rest on bottom 12. The weight of the sampling gauge 10 on guide pins 44 of actuator plate 43 causes valve lifter 46 to engage and open valve 40. Since water has initially been used to fill the cylinder 20, oil from layer 14 will flow into the cylinder 20 through openings 29 in top plate 21, and will displace water through inlet opening 33 and grooves 35. This displacement will continue until the interface level within cylinder 20 equals the depth of the surrounding water layer 15 in tank 11. To insure that the level of water inside cylinder 20 is equalized with the depth of water layer 15, sampling gauge 10 is left at rest on bottom 12 for a period of about 60 seconds. Longer times may be needed if the oil is heavy.

Sampling gauge 10 is then lifted from tank 11 by line 50. Initial upward movement of sampling gauge 10 causes bottom plate 23 to move upward in relation to actuator plate 43 (hence valve lifter 46) which allows spring 42 to bias valve 40 downward to close inlet opening 33. This traps the water in cylinder 20 and maintains the interface level which exists in cylinder 20 for observation, measurement, and analysis once the sampling gauge 10 is retrieved from tank 11. To aid in the measurement of the depth of layer 15, cylinder 20 may include calibrations thereon (not shown) which permits direct reading of the interface height in cylinder 20.

A unique feature of sampling gauge 10 is that its performance is not degraded by the existence of an emulsion layer between the oil and water. A sharp interface will be shown at the equivalent interface level, i.e. where the level would be if the water and oil had had sufficient time to separate completely. Thus, the interface shown in the cylinder 20 is a true representative measure of the actual depth of water layer 15 in tank 11.

Further, the principle of operation makes the design of sampling gauge 10 effective for virtually any diameter and length of cylinder 20, provided cylinder 20 is long enough to extend above the oil-water interface, or any emulsion layer, in tank 11 when sampling gauge 10 is on the tank bottom 12. It is also preferred that the diameter be large enough to allow for free flow of the liquid material. For example, a preferred sampling gauge 10 may incorporate a 2" O.D.×1¾" I.D. Plexiglas ® (Rohm & Haas Co.) cylinder, 20" long.

Figure 4:
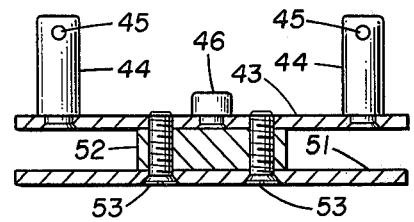
FIG. 4 is a section view of a modified valve actuator plate of the present invention.

In some instances, sludge or like matter may be present on bottom 12 of tank 11 which might interfere with the normal operation of sampling gauge 10. In such a case, valve actuator plate 43 may be modified as shown in FIG. 4. A foot plate 51 is spaced from actuator plate 43 by means of spacer member 52 and is connected thereto by means of screws 53 or the like. Thus, when sampling gauge 10 is lowered into tank 11, foot plate 51 will engage bottom 12 and grooves 35 (i.e. liquid passages) in bottom plate 23 will lie above the sludge layer when valve 40 is opened by lifter 46. Of course the thickness of spacer member 52 will vary in different instances depending on the thickness of the particular sludge layer involved.

Also, in some instances the depth of water level 15 in tank 11 may exceed the original length of cylinder 20. In addition to using a longer cylinder in the original assembly of sampling gauge 10, a sampling gauge having a shorter cylinder can be modified similarly as described above by attaching extension members (similar to spacer members 52 in FIG. 4), e.g. up to 2 feet in length, to bottom plate 43 so that sampling gauge 10 is elevated sufficiently when on the bottom of the container to measure the water depth. The interface depth in cylinder 20 plus the length of the extension will equal the depth of the measured water level.

What is claimed is:

1. A liquid sampling apparatus for obtaining a liquid sample from near the bottom of a liquid-filled container comprising:
   a sample chamber normally open at its upper end;
   means for raising and lowering said sample chamber into and out of said liquid-filled container;
   a bottom closure member affixed to the lower end of said sample chamber to prevent liquid flow into said sample chamber; said bottom member having an inlet opening therethrough;
   valve support means mounted on said bottom closure member;
   a valve slidably mounted in said valve support means and positioned to engage said inlet opening in said bottom closure member when said valve is in a closed position;
   spring means for normally biasing said valve to said closed position;
   actuating means for opening said valve means to permit liquid flow through said inlet opening into said sample chamber when said liquid sampling apparatus engages the bottom of said liquid-filled container and to close said valve means when said liquid sampling apparatus is lifted from engagement with said bottom of said liquid container; and
   said actuating means comprising an actuator plate, means for slidably mounting said actuator plate on said bottom closure member, and a valve lifter mounted on the upper surface of said actuator plate and adapted to engage and lift said valve to an open position when said actuator plate is moved upward relative to said bottom closure member.

2. The liquid sampling apparatus of claim 1 wherein said sample chamber comprises:
   a cylinder of transparent material.

3. The liquid sampling apparatus of claim 1 including:
   a top closure member affixed to said upper end of said sample chamber, said top closure member having openings therethrough to permit liquid flow through said openings into and out of said sample chamber.

4. The liquid sampling apparatus of claim 3 wherein said sample chamber comprises:
   a cylinder of transparent material.

5. The liquid sampling apparatus of claim 4 wherein:
   said top closure member comprises a top plate having a circumferential groove on its lower surface adapted to receive the upper end of said cylinder;
   said bottom closure member comprises a bottom plate having a circumferential groove on its upper surface adapted to receive the lower end of said cylinder;
   and including:
   tie rod means extending between said top and bottom plates for affixing said top and bottom plates to said cylinder.

6. A liquid sampling apparatus for obtaining a liquid sample from near the bottom of a liquid-filled container comprising:
   a sample chamber comprising a cylinder of transparent material;
   a top closure member affixed to the upper end of said sample chamber, said top closure member having openings therethrough to permit liquid flow through said openings into and out of said sample chamber, and comprising a top plate having a circumferential groove on its lower surface adapted to receive the upper end of said cylinder;

means for raising and lowering said sample chamber into and out of said liquid-filled container;

a bottom closure member affixed to the lower end of said sample chamber to prevent liquid flow into said sample chamber, said bottom closure member comprising an inlet opening therethrough and a bottom plate having a circumferential groove on its upper surface attached to receive the lower end of said cylinder;

tie rod means extending between said top and bottom plates for affixing said top and bottom plates to said cylinder;

valve support means mounted on said bottom closure member;

a valve slidably mounted in said valve support means and positioned to engage said inlet opening in said bottom closure member when said valve is in a closed position;

spring means for normally biasing said valve to said closed position;

actuating means for opening said valve means to permit liquid flow through said inlet opening into said sample chamber when said liquid sampling apparatus engages the bottom of said liquid-filled container and to close said valve means when said liquid sampling apparatus is lifted from engagement with said bottom of said liquid container; and said actuator means comprising an actuator plate, means for slidably mounting said actuator plate on said bottom closure member, and a valve lifter mounted on the upper surface of said actuator plate and adapted to engage and lift said valve to an open position when said actuator plate is moved upward relative to said bottom closure member.

7. The liquid sampling apparatus of claim 6 wherein said means for raising and lowering said sample chamber comprises:

an eye affixed to the upper surface of said top plate; and a line attached to said eye.

8. The liquid sampling apparatus of claim 1 wherein said container is a cargo tank of a tanker ship.

9. A method of measuring the depth of a bottom water layer in a container having oil and water layers comprising the steps of:

initially filling a sample chamber of a liquid sampling apparatus with water, said apparatus being open at its upper end to said sample chamber;

lowering said apparatus into said container;

positioning said apparatus on a bottom portion of said container;

actuating a valve means at a lower end of said apparatus whereby an inlet opening of a bottom member of said apparatus is opened to permit fluid to pass through said inlet opening of said bottom member to said sample chamber;

allowing said fluid in said sample chamber to reach equilibrium whereby the depth of said water layer measured by said apparatus becomes substantially the same as the depth of said water layer in said container;

withdrawing said apparatus from said container; and measuring the depth of said water layer from said apparatus.

10. The method of claim 9 wherein said container is a cargo tank of a tanker ship.

* * * * *